United States Patent [19]

Teicher et al.

[11] Patent Number: 5,451,213
[45] Date of Patent: Sep. 19, 1995

[54] PROTECTIVE DEVICE FOR SYRINGE NEEDLES

[75] Inventors: Mordechai Teicher, Kfar Saba; Itzhak Liechtenstein, Haifa, both of Israel

[73] Assignee: Log Plastic Products, Ashdod Ya'akov Ichud, Israel

[21] Appl. No.: 251,026

[22] Filed: May 31, 1994

[51] Int. Cl.⁶ ............................................. A61M 5/32
[52] U.S. Cl. ...................................... 604/192; 604/263
[58] Field of Search ............... 604/192, 187, 110, 263; 206/365

[56] References Cited

U.S. PATENT DOCUMENTS

| | | | |
|---|---|---|---|
| 4,610,667 | 9/1986 | Pedicano et al. | 604/192 |
| 4,836,373 | 6/1989 | Goldman | 206/366 |
| 4,986,817 | 1/1991 | Code | 604/263 X |
| 5,078,696 | 1/1992 | Nedbaluk | 604/192 |
| 5,183,469 | 2/1993 | Capaccio | 604/192 |
| 5,347,078 | 9/1994 | Eckels | 604/192 X |

*Primary Examiner*—John D. Yasko
*Attorney, Agent, or Firm*—Ladas & Parry

[57] ABSTRACT

A disposable protective device for syringe needles includes a sheath open at one end for receiving a syringe needle, a needle retainer formation within the sheath engageable with the hub of a needle when inserted into the sheath for retaining the needle within the sheath, and a supporting member cooperable with the sheath for stably supporting the sheath in an upstanding position on a flat supporting surface to enable manually inserting a syringe needle into the sheath without manually gripping the sheath.

10 Claims, 8 Drawing Sheets

PROTECTIVE DEVICE FOR SYRINGE NEEDLES

FIELD AND BACKGROUND OF THE INVENTION

The present invention relates to a protective device for syringe needles, and particularly to such a device which may be used for disposing contaminated syringe needles without the danger of contact by personnel.

Contaminated syringe needles pose a very serious danger to the health of personnel who handle the syringe needles, and many techniques have been proposed to protect such personnel from direct contact with contaminated needles. Many of the proposed solutions provide an arrangement for retracting the contaminated needle into the syringe so that both can be disposed at one time without coming into contact with the needle; such arrangements, however, require complete redesign of the syringe itself and are not usable with conventional syringe constructions. Other known arrangements provide a sheath for application to the contaminated needle, as described for example in U.S. Pat. No. 4,610,667; such known arrangements, however, generally require the use of two hands, one for holding the syringe and the other for holding the sheath. This is not only inconvenient for the attendant, but also poses a serious danger that the attendant may inadvertently bring the needle into contact with the attendant's hand holding the sheath at the time the needle is inserted into the sheath.

OBJECTS AND BRIEF SUMMARY OF THE INVENTION

An object of the present invention is to provide a disposable protective device which can be applied in a convenient manner to cover and protect a syringe needle by using only the one hand holding the syringe, thereby eliminating the danger of bringing the syringe needle into contact with either hand of an attendant. Another object of the invention is to provide such a disposable protective device which also permits safe removal of a used needle from the syringe. A further object of the invention is to provide such a disposable protective device which may also function, not only as a sheath for a used needle, but also as part of the original packaging of the needle, thereby obviating the need for two sheaths and also ensuring the availability of a protective device according to the present invention when needed to dispose a used needle. A further object of the invention is to provide a protective device which is fully compatible with standard needles and syringes.

According to the present invention, there is provided a disposable protective device for syringe needles having a hub, comprising: a sheath open at one end for receiving a syringe needle through the open end; needle retainer means within the sheath engageable with the hub of a needle when inserted into the sheath for retaining the needle within the sheath; and a supporting member cooperable with the sheath for stably supporting the sheath in an upstanding position on a flat supporting surface to enable manually inserting a syringe needle into the sheath without manually gripping the sheath.

According to further features in the described preferred embodiments, the open end of the sheath is enlarged such as to facilitate the insertion of a needle into the sheath and to guide the needle to the end of the sheath opposite to its open end. More particularly, the open end of the sheath is in the shape of a funnel.

According to further features in some described embodiments, the supporting member is a flat base attached to the end of the sheath opposite to its open end. The flat base may be integrally formed with the sheath, or may be formed as a separate member from the sheath and attachable to the sheath.

According to further features in some described embodiments, the needle retainer means includes a locking formation formed at the open end of the sheath and engageable with the hub of a syringe needle when inserted into the sheath, the locking formation being constructed to permit movement of the syringe needle into the sheath but to prevent movement of the syringe needle in the opposite direction, to thereby irreversibly lock the needle within the sheath once inserted therein.

The needle retainer means may also include a releasable retainer formation engageable with the needle hub for releasably retaining the needle within the sheath when inserted therein.

A further embodiment is described wherein the supporting member includes a plurality of radially-extending, circumferentially-spaced ribs integrally formed with the sheath and terminating in flat bottom edges providing a stable support for the device on a flat horizontal surface.

A still further embodiment is described wherein the supporting member is pivotally mounted to an intermediate part of the sheath and is pivotal either to a non-operative position substantially aligned with the sheath, or to an operative position forming an acute angle with the sheath to provide, with the closed end of the sheath, a stable support for supporting the device on a flat horizontal surface.

As will be more particularly described below, a protective device constructed in accordance with the foregoing features may be conveniently applied to a syringe needle by using only the one hand holding the syringe needle, permits the safe removal of a used syringe needle from the syringe, may also be used not only for diposing a used syringe needle, but also as the original packaging of the syringe needle, and may be used with standard needles and syringes.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
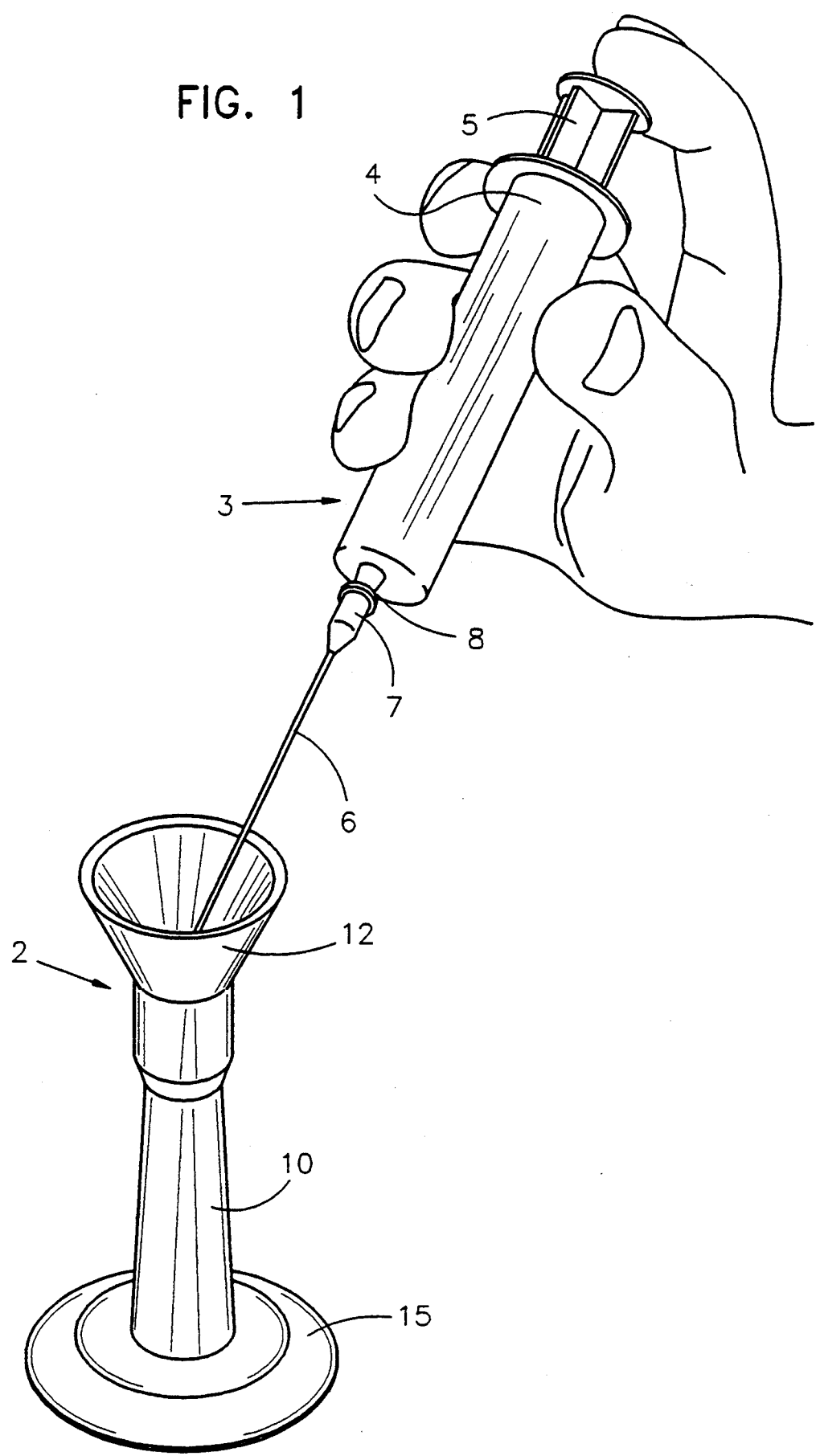
FIG. 1 is a pictorial illustration of one form of protective device for syringe needles and the manner a syringe needle is applied thereto.

The protective device illustrated in FIGS. 1-4, therein generally designated 2, is for use with a syringe, generally designated 3, of substantially conventional construction. The syringe includes a barrel assembly 4, a plunger assembly 5, and a needle 6 connected to the barrel assembly via a hub 7 formed with an annular rib 8.

Figure 2:
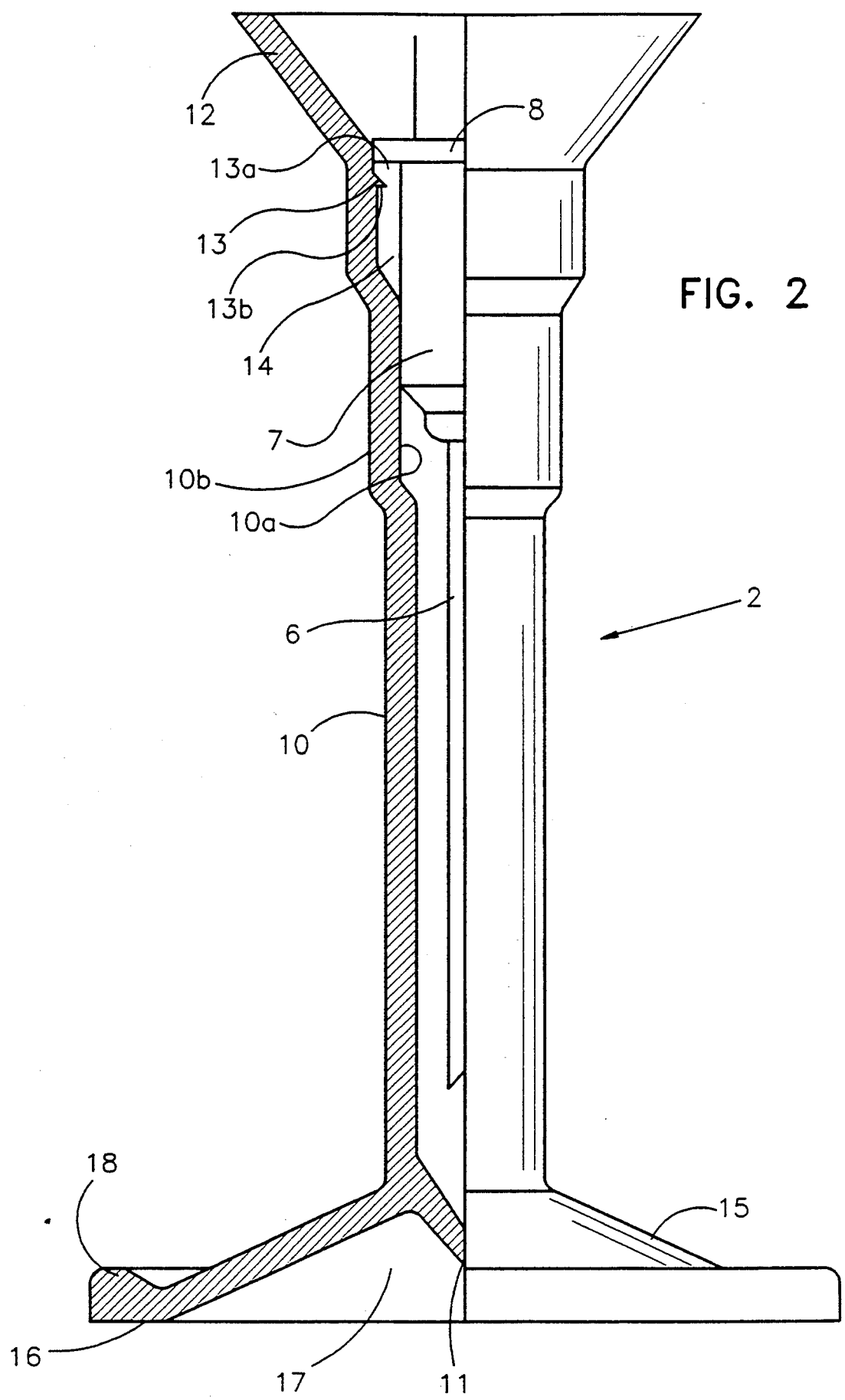
FIG. 2 is an enlarged side elevational view, partly in longitudinal section, illustrating the construction of the protective device of FIG. 1.
Figure 3:
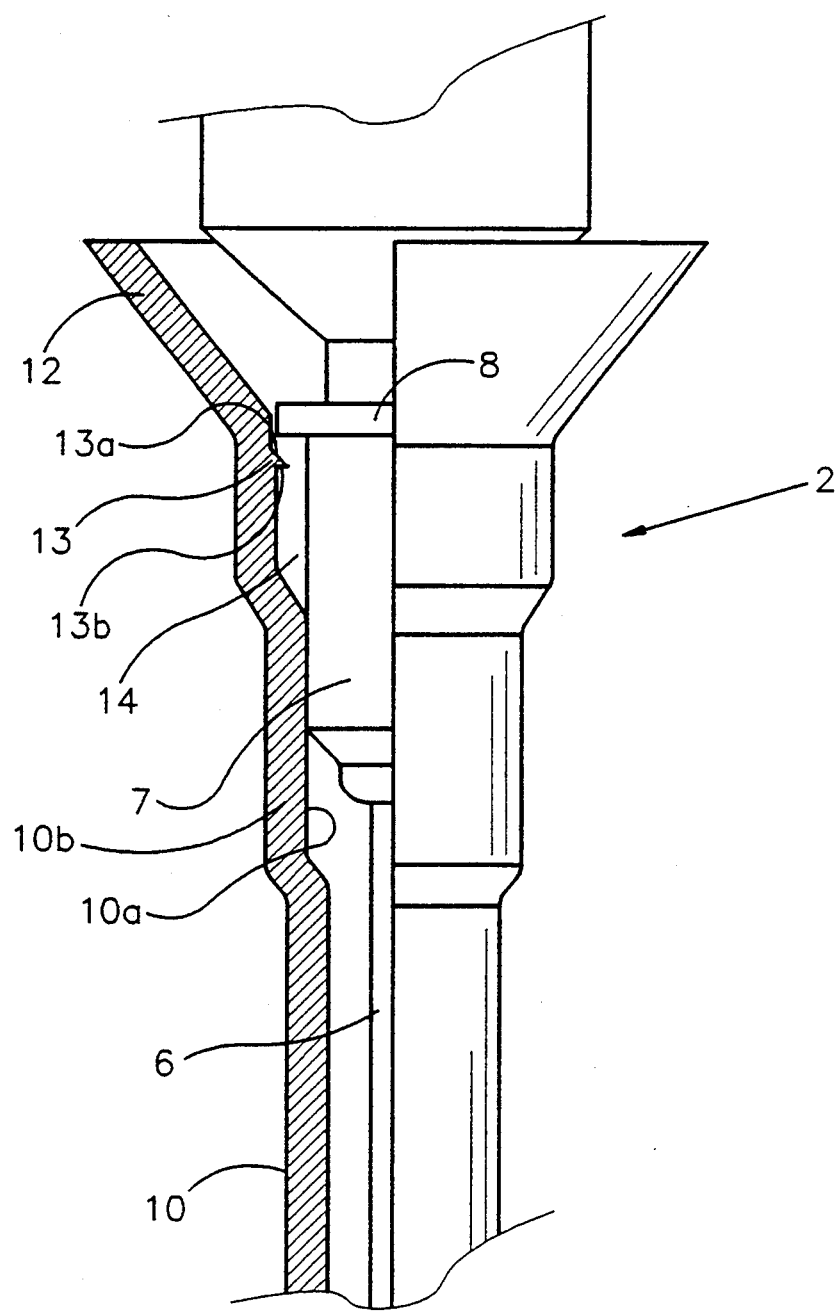
FIGS. 3 and 4 are enlarged fragmentary views of the protective device of FIG. 1 showing the syringe needle, respectively, in an unlocked position (FIG. 3) and a locked position (FIG. 4) within the protective device.
Figure 4:
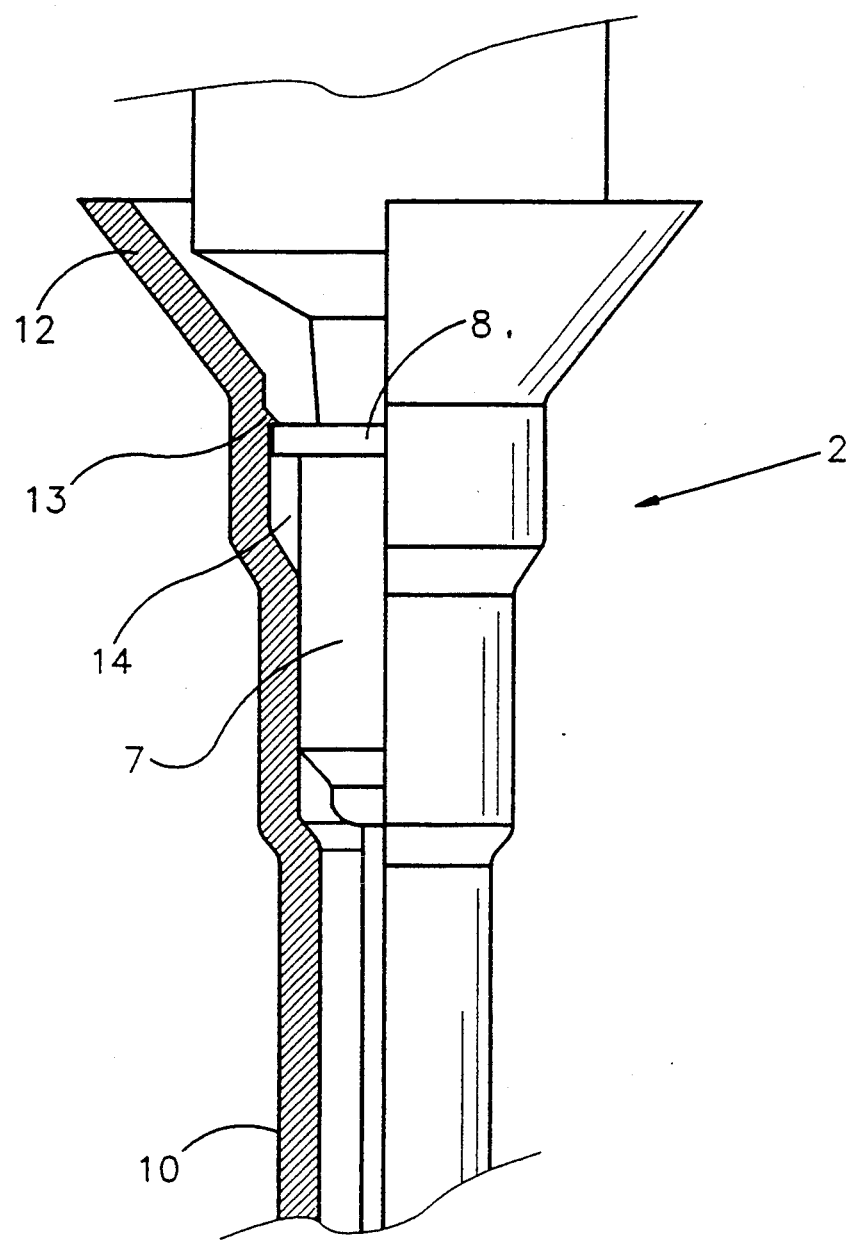

The protective device 2, as more particularly seen in FIG. 2, comprises a sheath 10 open at its upper end and closed at its lower end 11. The upper end of sheath 10 is formed with an inner diameter which is substantially the same as the outer diameter of the needle hub 7 so as to snugly receive the needle hub therein. The inner diameter of sheath 10, however, is substantially larger than that of the needle 6 to provide ample space between the needle and the inner face of the sheath, and thereby to facilitate the insertion of the needle into the sheath and also to decrease the possibility of contact between the needle and the inner face of the sheath, or of the penetration of the needle through the sheath, when the needle is inserted into the sheath.

The upper end of sheath 10 is formed with a guiding funnel 12 for guiding the syringe needle into the sheath.

The upper end of the sheath, particularly at its juncture with guiding funnel 12, is formed with a locking formation engageable with the hub 7, particularly its annular rib 8, for locking the syringe needle within the sheath. This locking formation comprises an annular shoulder 13 engageable with annular rib 8 of the needle hub 7. The outer face 13a of shoulder 13 is slanted with respect to the longitudinal axis LA of the sheath, to permit movement of the annular rib 8 of the needle hub 7 in the entering direction when inserting the needle 6 into the sheath. Annular shoulder 13 is further formed with an inner face 13b which is oriented perpendicularly to the longitudinal axis LA of the sheath 10 to prevent movement of the syringe needle and its hub in the opposite direction, thereby locking the needle within the sheath after it has been once introduced into the sheath.

The upper end of sheath 10 is further formed with an annular recess 14 inwardly of the annular shoulder 13 and of a size to accommodate the annular rib 8 of the needle hub 7 when the needle is inserted into the sheath 10.

Both the inner diameter and the outer diameter of sheath 10 are slightly increased at the upper end of the sheath, as shown at 10a and 10b, respectively, to accommodate the needle hub 7. The inner diameter 10a of the upper end of the sheath is preferably of slightly conical configuration, increasing in diameter towards the upper end of the sheath, to facilitate the entry of the needle hub into the sheath.

The protective device illustrated in FIGS. 1 and 2 further includes a supporting member in the form of an enlarged base 15 at the closed end of the sheath 10 and perpendicular to the sheath, for stably supporting the sheath on a flat supporting surface, such as a table top. This enables the syringe needle 6 to be inserted into the sheath without manually gripping the sheath.

Base 15 is of circular configuration of larger diameter than the diameter of the upper end of the guiding funnel at the open end of the sheath 10. The base includes a bottom face which is flat around its periphery, as shown at 16, and recessed at its center 17. The upper face of base 15 defines an annular fluid collecting channel 18 near the outer periphery of the base, for collecting any fluids that may be accidentally spilled or dripped onto the protective device 2.

The manner of using the protective device of FIGS. 1-4 will be apparent from FIG. 1. Thus, the enlarged base 15, and its flat bottom peripheral surface 16, enables the device to be stably supported on a flat horizontal surface, such as table top, with the sheath 10 extending vertically upwardly. After the user has operated the syringe 3, the contaminated needle 6 may be inserted through the guiding funnel 12 at the upper open end of the sheath 10 until the annular rib 8 of the needle hub 7 engages the upper slanted surface 13a of the annular locking shoulder 13. The user then presses down further to cause the annular rib 8 to snap into the annular recess 14 formed in the sheath 10, whereupon the needle is locked within the sheath and cannot be removed because of the perpendicular face 13b of the annular locking rib 13 engaging the outer face of the annular rib 8 of the needle hub 7. The protective device, including the needle 6 locked within it, may then be disposed without danger of coming into contact with the contaminated needle 6.

It will thus be seen that the illustrated device permits the needle to be inserted into the sheath with one hand, namely the hand holding the syringe 3 as shown in FIG. 1. This makes the insertion of the syringe needle into the sheath much more convenient and also reduces the possibility that the contaminated needle 6 may accidentally come into contact with the other hand of the user.

Figure 5:
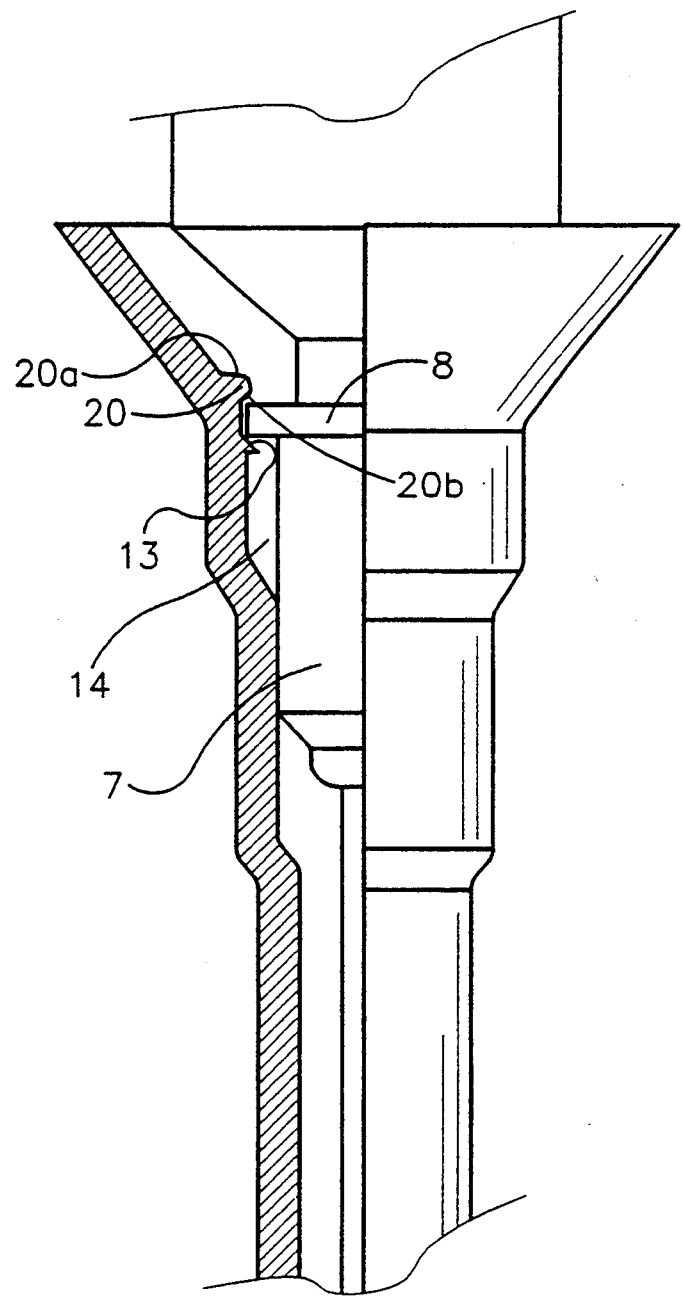
FIG. 5 is an enlarged view similar to that of FIG. 3 but illustrating a modification in the construction of the protective device.
Figure 6:
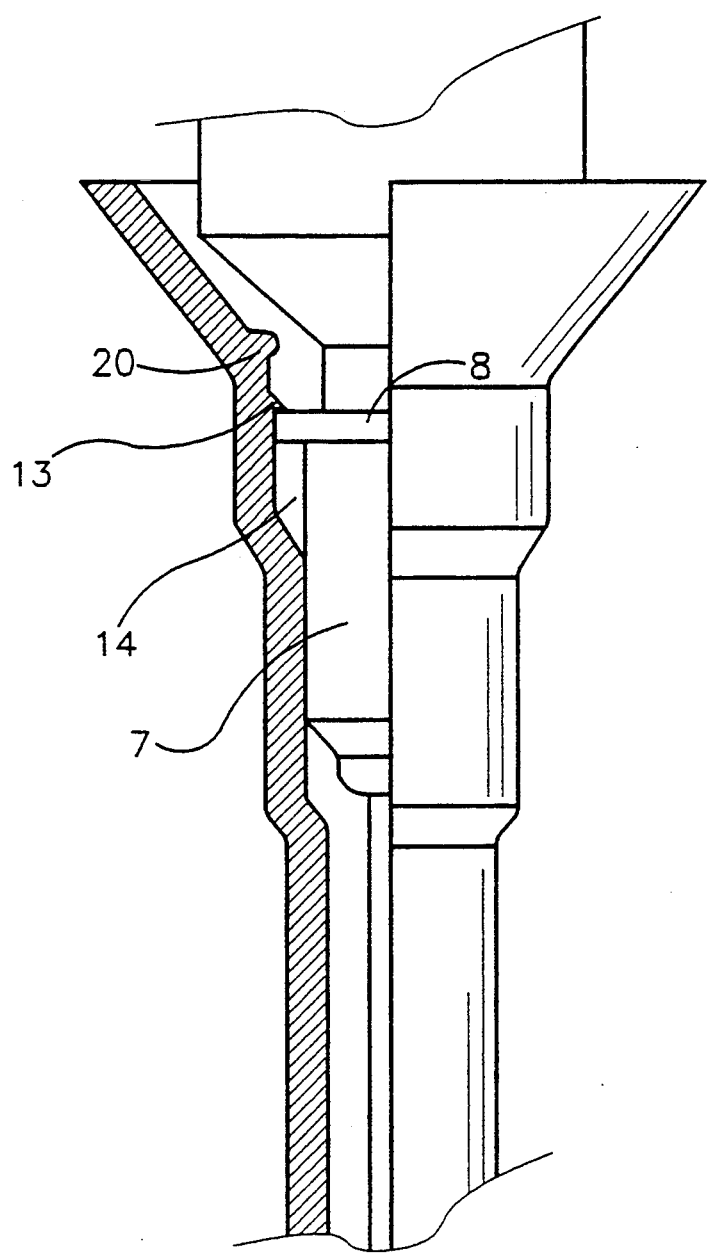
FIG. 6 is a view, similar to that of FIG. 5, but showing the syringe needle in its locked position within the protective device.

FIGS. 5 and 6 illustrate a modification in the construction of the protective device. In this modification, the open end of the sheath 10 is further formed with a retainer formation outwardly of the annular locking shoulder 13 engageable with the annular rib 8 of the needle hub for releasably retaining the needle within the sheath. This retainer formation is in the form of an annular rib 20 which is of curved, e.g., semi-spherical, configuration in cross-section. Rib 20 thus defines an outer face 20a slanted with respect to the sheath longitudinal axis LA and engagable by the annular rib 8 of the needle hub to permit entry of the needle into the sheath 10, and an inner face 20b which is also slanted with respect to the sheath longitudinal axis to thereby permit removal of the needle from the sheath.

Such a retainer formation enables the sheath to be used not only as a protective device for disposing a contaminated needle after use, but also as the original packaging for the needle before use. Thus, the needle, including its hub 7, would be inserted into the sheath 10 with the annular rib 8 of the hub located between the retainer rib 20 and the locking shoulder 13, and with the open end of the guiding funnel 12 closed. The whole package could then be sterilized. When the needle is to be used, it would be withdrawn from the sheath (this being permitted by the slanted underface 20b of the retainer rib 20), used for injection, and then reinserted into the same sheath. This time, however, the needle would be pressed further downwardly in the sheath to cause annular rib 8 of the needle hub 7 to snap past the locking shoulder 13, as shown in FIG. 6, whereupon the needle would be locked within the sheath for disposal.

Figure 7:
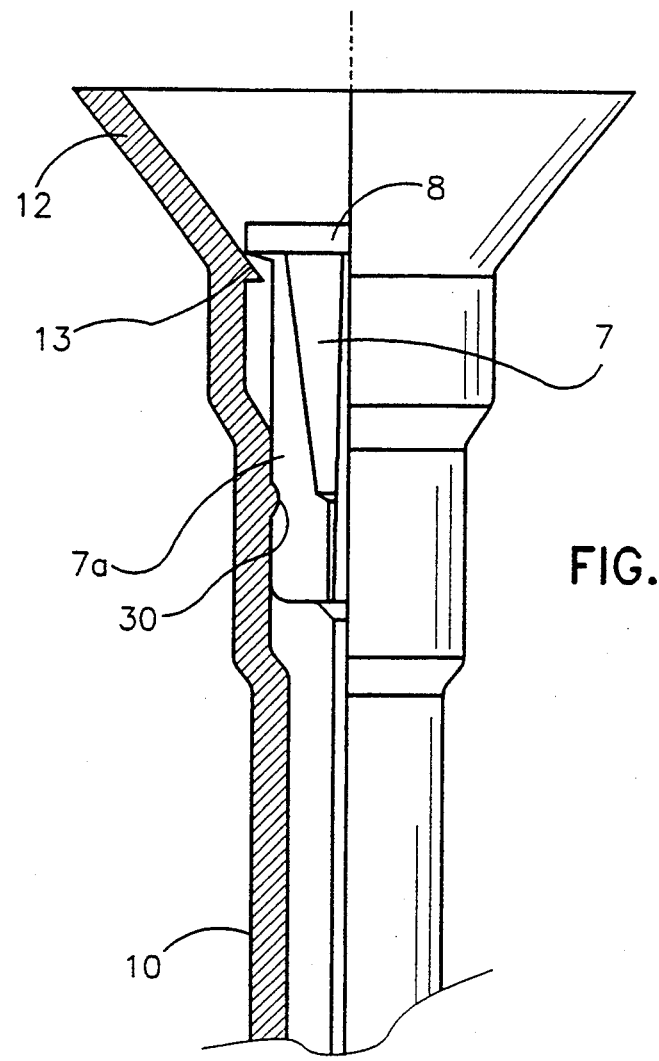
FIG. 7 is a side elevational view, partly in longitudinal section, illustrating another construction of protective device in accordance with the present invention.

FIG. 7 illustrates another construction of disposable protective device for use with a standard syringe needle in which the hub 7 is formed with a plurality of axially-extending, circumferentially-spaced ribs 7a. In this case, the annular locking shoulder 13 is formed at the open end of the sheath, at the juncture with the funnel 12, and the releasable retainer formation is in the form of an annular rib 30 inwardly of the annular locking shoulder 13, and releasably engageable with the outer edges of the hub axial ribs 7a. Thus, the syringe needle is releasably retained within the sheath by the friction between the annular rib 30 and the outer surface of the axial ribs 7a.

Figure 8:
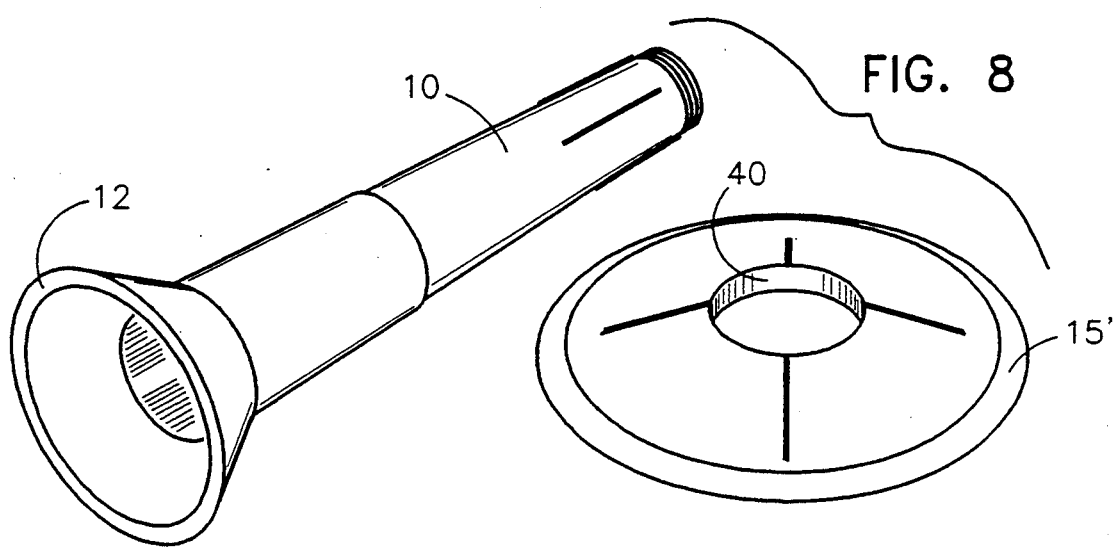
FIG. 8 illustrates the protective device of FIGS. 1-6, or that of FIG. 7, constructed with a removable base attachable to the sheath when the sheath is to be used.

FIG. 8 illustrates a variation in the construction of the protective device wherein the base, therein designated 15' is not integrally formed with the sheath 10 but rather is formed as a separate part, e.g., to provide a more compact package. In this modification, the base 15' may be provided with a center socket 40, to receive the closed end of the sheath 10 when the device is to be used for receiving the syringe needle and its hub in the manner described above. The sheath 10 may be attached to the base 15' in any convenient manner, e.g., by a friction fit, by a threaded fit, or by the use of an adhesive.

The variation illustrated in FIG. 8 is particularly useful where the original sheath package for the syringe needle is also to be used as the sheath for disposing a contaminated needle. In such case, it would be necessary to supply only the base 15', to be attached to the original sheath used for packaging the syringe needle when that sheath is also to be used for disposing a contaminated needle in the manner described above.

Figure 9:
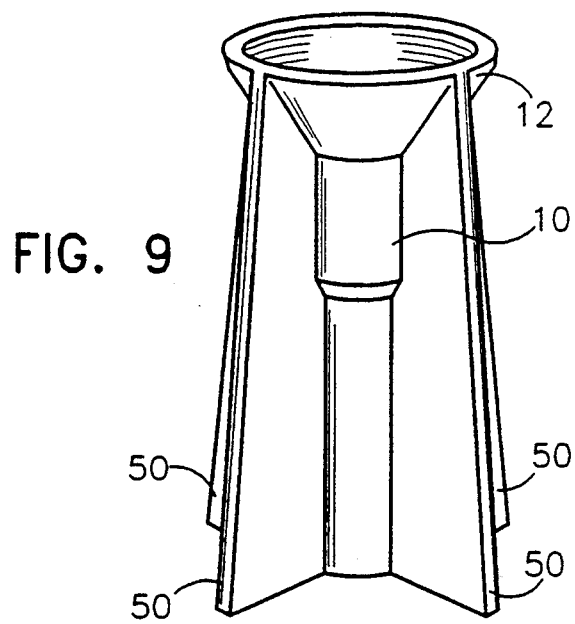
FIGS. 9 and 10 are side elevational views illustrating two further constructions of protective devices in connection with the present invention.

FIG. 9 illustrates a further construction wherein the supporting member for supporting the sheath is in the form of a a plurality (e.g., 4) of radially-extending, circumferentially-spaced ribs 50 integrally formed with the sheath and terminating in flat bottom edges 52 providing a stable support for the protective device on a flat horizontal surface. In the example illustrated in FIG. 9, ribs 50 extend for the complete length of the sheath 10 and have an increasing width, from the open end of the sheath formed with the guiding funnel 12, to the closed bottom end of the sheath.

Figure 10:
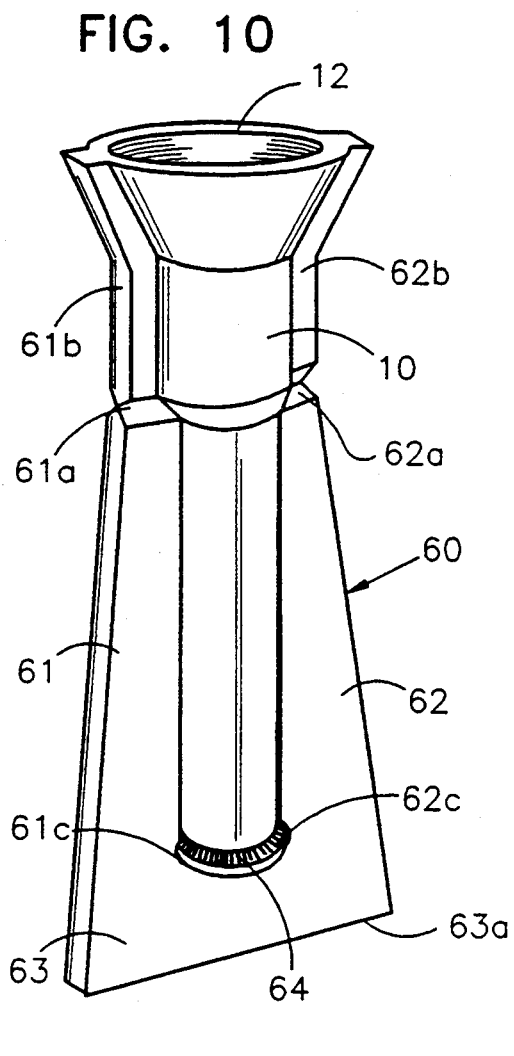
Figure 11:
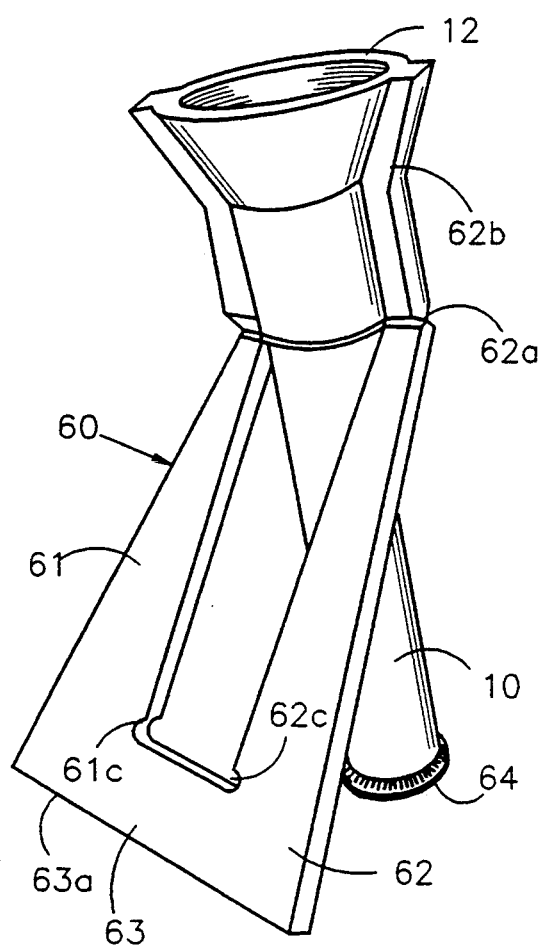
FIG. 11 illustrates the protective device of FIG. 10 in its operative position for receiving a needle after the needle has been contaminated.

FIGS. 10 and 11 illustrate a further construction wherein the supporting member, generally designated 60, is pivotally mounted to an intermediate part of the sheath 10 and is pivotal either to a non-operative position as illustrated in FIG. 10, or to an operative position as illustrated in FIG. 11. The device would normally be packaged with the supporting member 60 in its non-operative position (FIG. 10) substantially aligned with the sheath 10, and would be manually pivotted to its operative position (FIG. 11), in which it forms an acute angle with the sheath 10, to provide, with the closed end of the sheath, a stable support for supporting the device on a flat horizontal surface.

More particularly, supporting member 60 is in the form of a U-shaped strip of rigid material having a pair of parallel legs 61, 62 pivotally connected at one of their ends 61a, 62a, to the opposite sides of the sheath 10. The two parallel legs 61, 62 are joined together at their opposite ends to a cross-leg 63 having a flat bottom edge 63a engageable with the flat, horizontal supporting surface in the operative position of the U-shaped strip 60. The supporting strip 60 is preferably integrally formed with the sheath 10, e.g., with a pair of longitudinally-extending ribs 61b, 62b, integrally formed with the upper part of the sheath and with its guiding funnel 12, such that the pivotal connections 61a, 62a are integral hinges between the respective ends of the two legs 61, 62 and their respective ribs 61b, 62b.

Preferably, the closed bottom end of sheath 10 is formed with a slightly enlarged base 64, flattened at the bottom, to increase the stability of the support provided by the U-shaped strip 60 and the closed end of the sheath 10 in the operative position of the protective device. The junctures of legs 61 and 62 with the cross-leg 63 may be formed with corresponding slits 61c, 62c, for accommodating the thickened bottom 64 of the sheath 10.

While the invention has been described with respect to several preferred embodiments, it will be appreciated that these are set forth merely for purposes of example, and that many other variations, modifications and applications of the invention may be made.

We claim:

1. A disposable protective device for syringe needles having a hub, comprising:
   a sheath open at one end for receiving a syringe needle through said open end;
   needle retainer means within the sheath engageable with the hub of a needle when inserted into the sheath for retaining the needle within the sheath;
   and a supporting member cooperable with the sheath for stably supporting the sheath in an upstanding position on a flat supporting surface to enable manually inserting a syringe needle into the sheath without manually gripping the sheath;
   said needle retainer means comprising:
   a locking formation formed at the open end of the sheath and engageable with the hub of a syringe needle when inserted into the sheath, said locking formation being constructed to permit movement of a syringe needle into the sheath but to prevent the movement of the needle in the opposite direction to thereby lock the needle within the sheath once inserted therein;
   and a releasable retainer formation formed in the open end of the sheath and engageable with the hub of the needle inserted therein for releasably retaining the needle and the hub within the sheath when inserted therein;
   said releasable retainer formation being located to releasably engage the needle hub before the needle hub is engaged by said locking formation.

2. The device according to claim 1, wherein said open end of the sheath is enlarged such as to facilitate the insertion of a needle into the sheath and to guide the needle to the end of the sheath opposite to its open end.

3. The device according to claim 2, wherein said open end of the sheath is in the shape of a funnel.

4. The device according to claim 1, wherein said supporting member is a flat base attached to the end of the sheath opposite to its open end.

5. The device according to claim 4, wherein said base is integrally formed with said sheath.

6. The device according to claim 1, wherein said releasable retainer formation is formed at said open end of the sheath, and said locking formation is formed inwardly of the sheath from said releasable retainer formation.

7. The device according to claim 6, wherein said releasable retainer formation is an annular rib having a curved outer face formed at the open end of the sheath, and said locking formation is a shoulder formed inwardly of the sheath from said annular rib.

8. A disposable protective device for syringe needles having a hub, comprising:
   a sheath open at one end for receiving a syringe needle through said open end;
   a releasable retainer formation formed in the open end of the sheath and engageable with the hub of the needle inserted therein for releasably retaining the needle and the hub within the sheath when inserted therein;
   and a locking formation formed at the open end of the sheath and engageable with the hub of a syringe needle when inserted into the sheath, said locking formation being constructed to permit movement of a syringe needle into the sheath but to prevent the movement of the needle in the opposite direction to thereby lock the needle within the sheath once inserted therein;
   said releasable retained formation being located to releasably engage the needle hub before the needle hub is engaged by said locking formation.

9. The device according to claim 8, further comprising:
   a supporting member cooperable with the sheath for stably supporting the sheath in an upstanding position on a flat supporting surface to enable manually inserting a syringe needle into the sheath without manually gripping the sheath.

10. The device according to claim 8, wherein said open end of the sheath is enlarged such as to facilitate the insertion of a needle into the sheath and to guide the needle to the end of the sheath opposite to its open end.

* * * * *